United States Patent [19]

Greene, Jr.

[11] Patent Number: 4,660,388

[45] Date of Patent: Apr. 28, 1987

[54] COOLING COVER

[76] Inventor: George J. Greene, Jr., 616 N. Eldridge St., Houston, Tex. 77079

[21] Appl. No.: 780,280

[22] Filed: Sep. 26, 1985

Related U.S. Application Data

[63] Continuation-in-part of Ser. No. 613,913, May 24, 1984, abandoned.

[51] Int. Cl.[4] .......... A47K 13/00

[52] U.S. Cl. .......... 62/261; 5/485; 98/1; 165/46

[58] Field of Search .......... 62/261, 259.3; 5/485, 5/461; 165/46; 98/89, 1 R; 128/400, 402

[56] References Cited

U.S. PATENT DOCUMENTS

| | | | |
|---|---|---|---|
| 1,489,308 | 4/1924 | Cox | 5/461 |
| 1,568,471 | 1/1926 | Roemer | 98/1 X |
| 2,093,834 | 9/1937 | Gaugler | 128/402 X |
| 2,897,741 | 8/1959 | Mauch | 98/1 |
| 3,345,641 | 10/1967 | Jennings | 128/402 X |
| 3,678,520 | 7/1972 | Evans | 5/453 |

*Primary Examiner*—William E. Wayner
*Attorney, Agent, or Firm*—Vinson & Elkins

[57] ABSTRACT

A cooling cover (10) has an air inflatable pad (16) which may be positioned within a pocket (20) of a coverlet (18). The pad (16) formed of air impermeable material has plenum chambers (28) at opposite ends thereof, and a plurality of individual longitudinally extending passages (26) extend between the plenum chambers (28). Openings or air orifices (34) of a non-uniform pattern in the lower rounded surfaces of the inflatable pad (16) direct cooling air in a plurality of small air jets onto the body of a user of the cooling cover (10). A source of cool air (21) is connected to the inlet (30) for a plenum chamber (28) to deliver cool air to the pad (16).

5 Claims, 9 Drawing Figures

COOLING COVER

CROSS REFERENCE TO RELATED APPLICATION

This application is a continuation-in-part of application Ser. No. 613,913 filed May 24, 1984.

BACKGROUND

Individual cooling suits and blankets have been attempted to provide cooling of people. Much of the work on this type of equipment has been done in the design of suits to be worn in space. In these prior art devices, cooling is accomplished by circulating a cooling liquid through cooling coils in the suit and supplying cooling air to a helmet to assure the supply of a cool air for breathing and cooling of the individual's face. A typical example of this type of suit is disclosed in U.S. Pat. No. 4,095,593. A suit to be worn during operations in a hospital is shown in U.S. Pat. No. 3,738,367 and includes tubes through which cooling liquid from a hyperthermia machine is circulated.

Another type of suit is shown in U.S. Pat. No. 3,174,300 which recirculates air by a blower carried in the suit through a carbon dioxide absorber and a coolant tank. The garmet shown in U.S. Pat. No. 3,479,838 utilizes a reduced pressure to cause water to boil in order to provide body cooling. A heat treating garment is shown in U.S. Pat. No. 3,610,251 which flows hot air into a baglike garment having apertures in the wrist or shoulders to allow escape of the hot air.

The R. S. Gaugler U.S. Pat. No. 2,093,834 discloses a refrigerating apparatus which can be used as a bed cover or as a garment. The cooling air or treating medium is supplied to an enclosure formed of sheeting and diffuses through the sheeting to cool the body of the individual under the apparatus.

None of these prior structures provide a simple structure which is suitable to cool an individual over a substantial portion of his body while he is asleep.

SUMMARY

The present invention provides a cooling cover to be used to cool an individual while sleeping or resting and includes a pad formed of an air impermeable material defining an air distribution chamber. The air distribution chamber has a plurality of longitudinal passages extending between transverse plenum chambers at each end of the pad, and an air inlet connects to the plenum chamber at the foot of the pad. The longitudinally extending air passages are defined by lower rounded surfaces which have openings or apertures therein spaced from the body of an individual and arranged to direct cool air onto the individual in a jet action.

A preferred source of cool air is a refrigeration or air conditioning system which includes a blower to cause the air to flow in heat exchange with the refrigeration system, and means for delivering the cooled air from the refrigeration system to the air distribution chamber inlet. A coverlet formed of a porous material has a pouch or pocket to receive the pad and air discharged from the apertures of the distribution chamber is diffused slightly by the porous material of the coverlet to keep the cool air flow from impacting an objectionable jet streams on the body of a user. Although some diffusing of the jet stream is desirable, an important part of this concept of cooling is to rely heavily upon the velocity of the air stream to enhance the cooling effect, thereby reducing the need for temperature depression and additional BTU cooling capacity.

An object of the present invention is to provide an improved cooling cover for a human body or individual which is effective for cooling the individual while sleeping or resting.

Another object is to provide an improved cooling cover for a human body which is relatively simple in construction, reasonable in cost, and can be operated with a portable power supply.

A further object is to provide an improved cooling cover for sleeping in hot environments which is efficient by exposing the body skin to a meaningful air velocity, but at the same time does not expose the user to jets of uncomfortably cool air.

DESCRIPTION OF THE DRAWINGS

These and other objects and advantages are hereinafter set forth and explained with reference to the drawings wherein.

BRIEF DESCRIPTION OF THE PREFERRED EMBODIMENT

Figure 1:
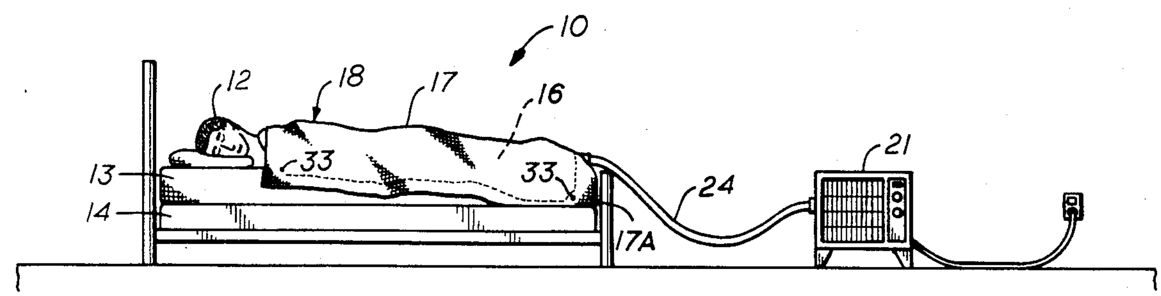
FIG. 1 is an elevational view, partly schematic, of the improved cooling apparatus of the present invention including an outer coverlet and an inner pad contained therein having an air distribution chamber.

The improved cooling cover of the present invention is indicated generally at 10 in FIG. 1 covering an individual or person 12 positioned on a mattress 13 of bed 14. Cooling cover 10 includes a pair of inner pads 16 positioned within an outer coverlet 18. Pads 16 form air distribution chambers and each pad 16 as shown in FIGS. 2–5 is preferably formed of an air impermeable heat bondable material such as polyethylene, polyvinylchloride, or other similar material.

Figure 6:
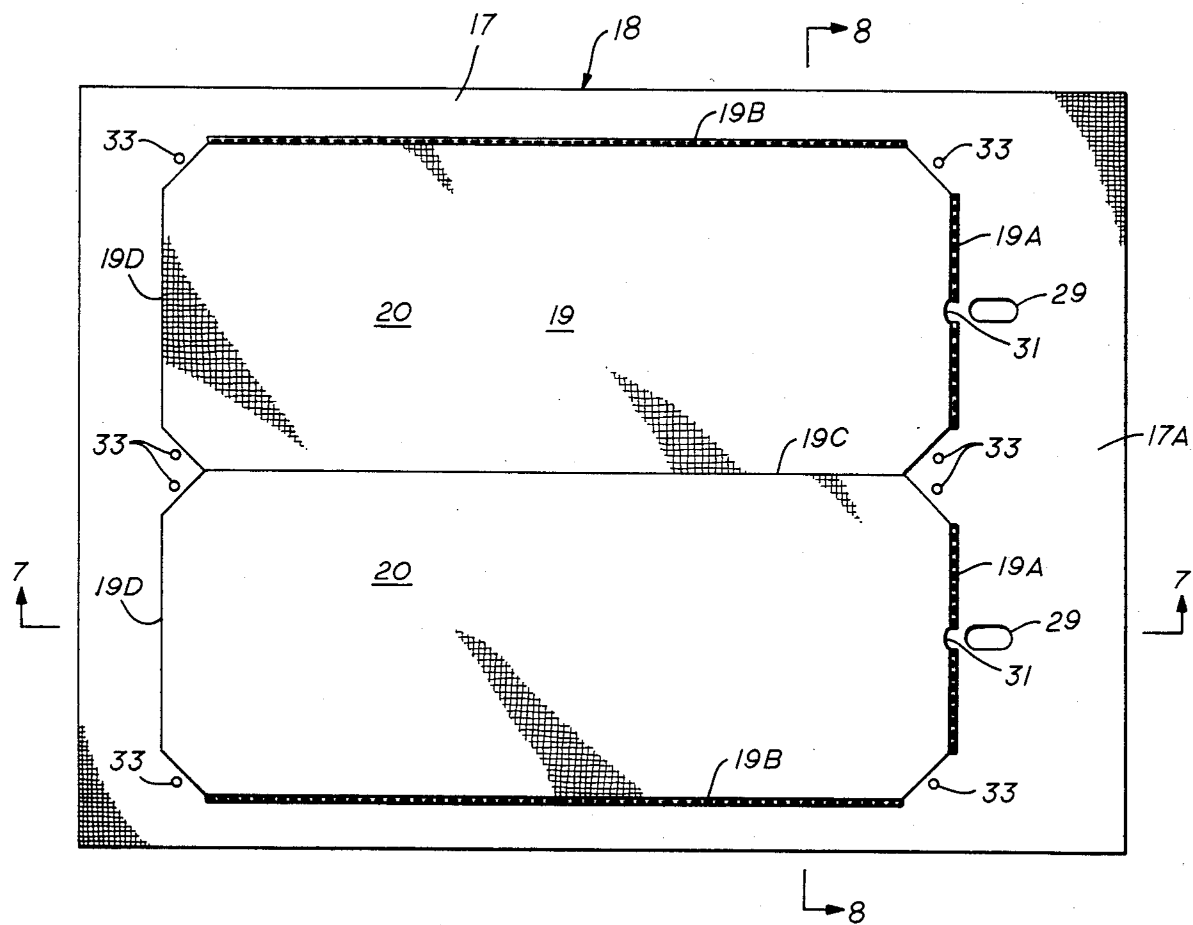
FIG. 6 is a plan of the underside of the outer coverlet having pockets to receive the pads.
Figure 7:
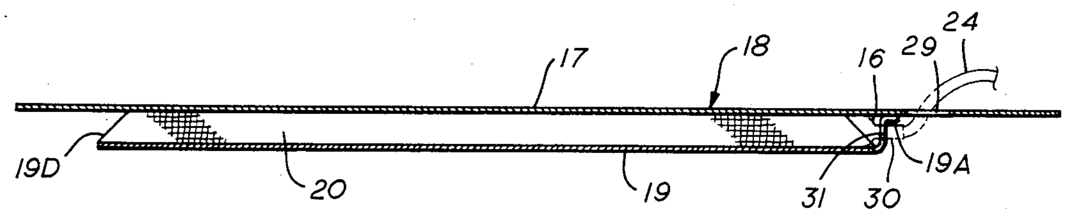
FIG. 7 is a sectional view of the coverlet taken along line 7—7 of FIG. 6 with the inner pad shown in broken lines.
Figure 8:
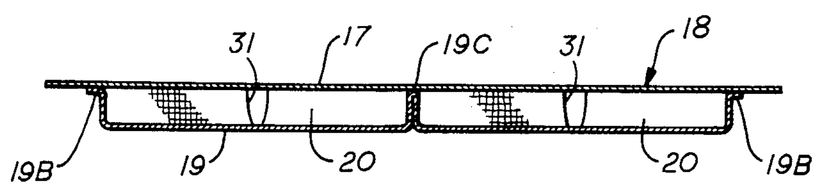
FIG. 8 is a sectional view of the coverlet taken along line 8—8 of FIG. 6.

Outer coverlet 18 as shown in FIGS. 6–8 includes an outer sheet 17 which may be formed, if desired, of an air permeable or porous material such as cotton; and an inner spaced sheet 19 which is always formed of an air permeable or porous material. Inner sheet 19 which is normally placed adjacent the body of a user is secured at one end 19A, sides 19B and intermediate portion 19C to sheet 17. The other end 19D of sheet 19 is open and spaced from sheet 17 thereby to define a pair of identical porous pockets or pouches 20 arranged in side-by-side relation. Each pouch 20 receives an inner pad 16 within open end 19D. A source of cool air such as cool air generator 21 is connected to a flexible hose or conduit 24 and has a suitable blower for delivering cool air to inner pads 16.

Figure 2:
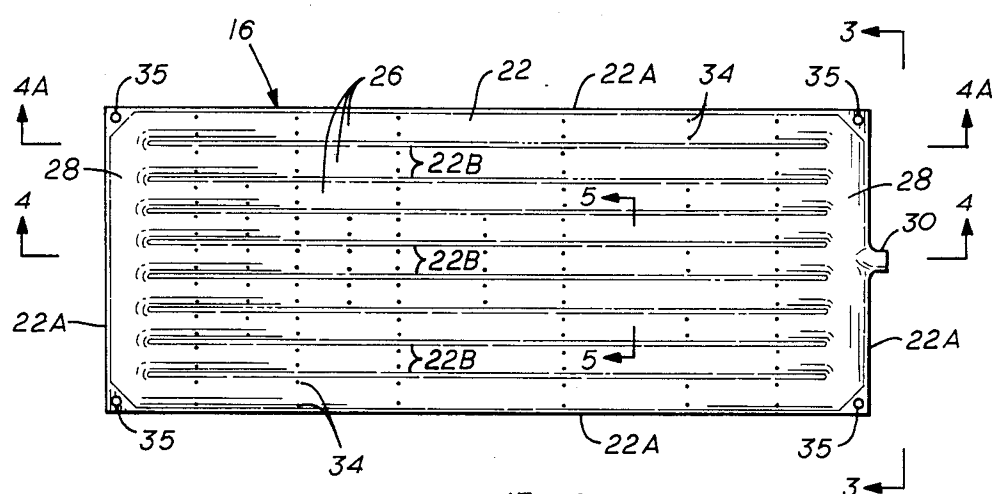
FIG. 2 is a view of the underside of the inner pad forming the air distribution chamber of the present invention.
Figure 3:
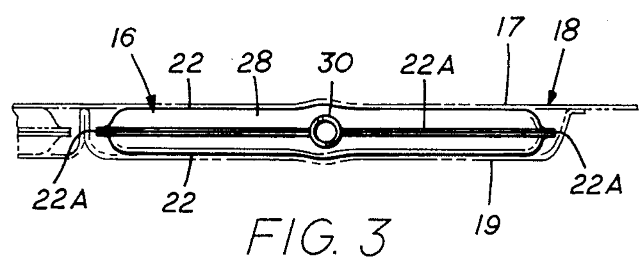
FIG. 3 is a elevational view of the inner pad taken along line 3—3 in FIG. 2.
Figure 4:
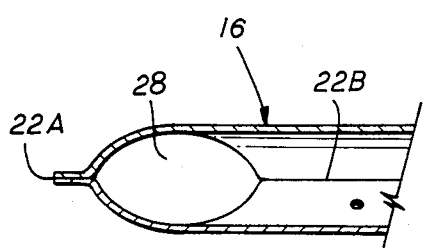
FIG. 4 is a sectional view of the inner pad taken along line 4—4 in FIG. 2.
Figure 4:
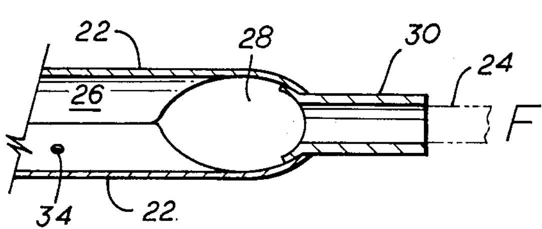
Figure 4A:
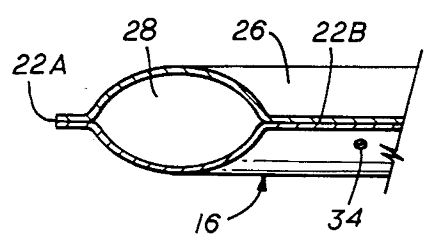
FIG. 4A is a sectional view of the inner pad taken along line 4A—4A in FIG. 2.
Figure 4A:
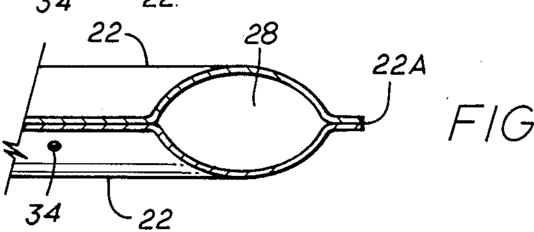

Each inner pad 16 which forms the air distribution chamber as shown in FIGS. 2, 3 and 4, is formed of two sheets of air impermeable material 22 as set forth above which are bonded together at their outer edges 22A. Also, intermediate portions 22B are suitably joined, as by bonding, to form a plurality of longitudinally extending air passages 26 extending from transversely extending plenum chambers 28 at each end. An air inlet 30 is positioned at the end of each pad 16 in communication with plenum chamer 28 to supply air to air passages 26.

Coverlet 18 has an end marginal portion 17A which extends beyond upper sheet 19 and beyond porous pouches 20 in which inner pads 16 are positioned. End portion 17A may be folded under the feet of individual 12 or be tucked under mattress 13 on bed 14 to provide a selective positioning of pads 16 and the air distribution chambers thereof on the individual. Coverlet 18 has suitable openings 29 and 31 to receive flexible hose 24 for connection to inlet 30 thereby to provide cool air to air passages 26 from cool air generator 21. Snap fasteners 33 on outer sheet 17 may engage interfitting fasteners 35 on pads 16 to hold pads 16 in place within pockets 20.

Figure 5:
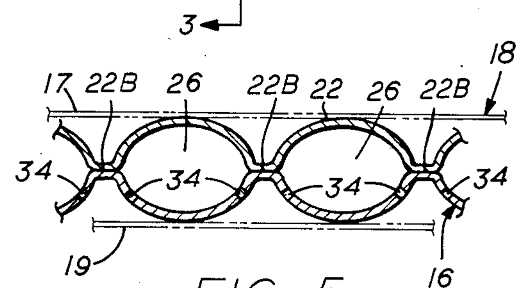
FIG. 5 is a sectional view of the inner pad taken along line 5—5 in FIG. 2 to illustrate the air distribution chamber apertures.

Each of the longitudinally extending air passages defines a lower rounded surface which is provided with a plurality of apertures 34 positioned as best shown in FIG. 5 so that the resting of inner pad 16 on the individual does not block the flow through any of the apertures 34 since apertures 34 are spaced from the body of the individual. Inner pad 16 is inflatable and a generally uniform pressure is provided. A predetermined arrangement of apertures 34 which form air orifices for pad 16 directs the air to predetermined areas of the body. Thus, a non-uniform distribution of apertures 34 permits a relatively high cooling efficiency.

It has been discovered that the jetting of the cool air through the apertures 34 at a velocity of not less than thirty feet per second results in very substantially improved cooling as compared to air diffusion through a sheet or cover. Also, each pad 16 would have approximately one hundred (100) one-eighth inch diameter apertures 34.

Further, it has been found that a cooling capacity of cool air generator 21 should be approximately 650 BTU/hour per person being cooled. This will provide an ambient air cooling at the source between 20° and 25° F. with a reduction of 18° F. at the body of the individual for cooling with ambient air temperature above 90° F. The air flow onto an individual is preferred to be in the range of 20 to 35 cubic feet per minute. A pressure of 0.4 to 0.9 inches of water is maintained in pad 16 to control the optimum air velocity and to support the shape of pad 16. An electric power consumption of between 130 and 175 watts per person allows a 300 to 350 watt generator to service a double unit as shown in FIG. 6.

It is suggested that the evaporator coil in the cool air generator be located above the vertical midpoint of the condenser unit so that gravity causes condensed moisture from the evaporator coil to flow to the hot condenser coil for evaporation and thus to increase the efficiency of the unit under high humidity conditions.

While the preferred embodiment of coverlet 18 is illustrated in FIGS. 6–8 as having a pair of pouches 20 for a pair of pads 16, it is to be understood that a single pad 16 and single porous pouch 20 could be provided if desired.

While preferred embodiments of the present invention have been illustrated in detail, it is apparent that modifications and adaptations of the preferred embodiments will occur to those skilled in the art. However, it is to be expressly understood that such modifications and adaptations are within the spirit and scope of the present invention as set forth in the following claims.

What is claimed is:

1. A generally rectangular cooling cover adapted to be positioned over a human body in a prone position; said cooling cover comprising;

a coverlet having an outer sheet, an inner porous pouch attached to the outer sheet, and an inner pad within the porous pouch;

said inner pad including a pair of upper and lower sheets formed of an air impermeable material with the upper sheet adjacent the coverlet and the lower sheet adjacent the porous pouch, said sheets secured to each other along their outer edges to form an air distribution chamber therebetween, and secured to each other along a plurality of parallel intermediate portions extending lengthwise between the ends of the sheets for a major portion thereof to form a plurality of separate longitudinally extending air passages there-between having lower rounded surfaces, a plenum chamber extending transversely of the pad at each end thereof in fluid communication with said longitudinally extending air passages; and a cool air inlet at one end of said inner pad, said coverlet having an opening therein in alignment with said inlet of said pad adapted to receive a source of cool air for connection to said inlet;

said lower rounded surfaces having a plurality of apertures along the length thereof at locations other than the lowermost portion of said rounded surfaces and in fluid communication with said longitudinally extending passages whereby cool air may be discharged as small jets through said apertures at an angular relation to a vertical plane for diffusing through the porous pouch to contact a large area of the body cooled.

2. A cooling cover as set forth in claim 1 wherein said outer sheet of said coverlet has fasteners thereon adjacent the corners of said pad, and said pad has interfitting fasteners thereby to releasably secure said pad within the pocket of said coverlet.

3. A cooling cover as set forth in claim 1 wherein said outer sheet of said coverlet and said pouch have aligned openings therein adapted to receive a flexible hose from said source of cool air for connection to said cool air inlet of said pad, thereby to supply cool air to said pad.

4. A cooling cover as set forth in claim 1 wherein said upper and lower sheets of said inner pad are formed of heat bondable plastic material.

5. Air conditioning means for a human body comprising:

a general rectangular cooling cover adapted to be positioned over the human body in a prone position, said cooling cover including a coverlet having an outer sheet, an inner porous pouch attached to the outer sheet, and an inner pad within the porous pouch; said inner pad including a pair of upper and lower sheets formed of an air impermeable material with the upper sheet adjacent the coverlet and the lower sheet adjacent said porous pouch, said sheets secured to each other along the outer edges to form an air distribution chamber therebetween, and secured to each other along a plurality of parallel intermediate portions extending lengthwise between the ends of the sheets for a major portion thereof to form rounded surfaces defining a plurality of separate longitudinally extending air passages;

a plenum chamber extending transversely of said pad at each end thereof in fluid communication with said longitudinal extending air passages, said rounded surfaces having a plurality of apertures therein for discharging cool air therethrough as small jets for diffusing through the air permeable porous pouch for contacting the human body, said apertures being arranged in a non-uniform manner with air being discharged therefrom at a velocity in a range between 30 and 50 feet per second;

a cool air inlet at one end of said inner pad in fluid communication with the associated plenum chamber at said one end, said coverlet having an opening adjacent said cool air inlet;

a source of cool air; and means extending through said opening in said coverlet to said inlet to connect the source of cool air to said air inlet for inflating the inflatable pad and providing air to said apertures for discharge therefrom, said source of cool air having a capacity of approximately 650 BTU/hour per person.

* * * * *